United States Patent [19]
Kimura

[11] Patent Number: 5,151,279
[45] Date of Patent: Sep. 29, 1992

[54] METHOD FOR MAKING RESIN DENTAL PLATES AND FLASKS

[76] Inventor: Hiroshi Kimura, No. 9-12, 5 Chome, Minamikasugaoka, Ibaraki-shi, Osaka, Japan

[21] Appl. No.: 758,510

[22] Filed: Sep. 6, 1991

Related U.S. Application Data

[63] Continuation of Ser. No. 430,573, Nov. 1, 1989, abandoned.

[30] Foreign Application Priority Data

Nov. 2, 1988 [JP] Japan .................. 63-276088

[51] Int. Cl.$^5$ .............................. B29C 45/18
[52] U.S. Cl. ..................... 425/178; 249/54; 425/180; 425/185; 425/567
[58] Field of Search ............ 425/812, DIG. 11, 2, 425/174, 175, 178, 180, 544, 567, 376.1, 569, 185; 249/54, 55, 82; 264/16, 17, 18, 19, 20

[56] References Cited

U.S. PATENT DOCUMENTS

| | | | |
|---|---|---|---|
| 68,548 | 9/1867 | Bean | 425/180 |
| 283,487 | 8/1883 | Housel | 425/180 |
| 1,575,688 | 3/1926 | Joannides | 425/180 |
| 2,341,991 | 2/1944 | Jackson | 425/180 |
| 2,660,758 | 12/1953 | Hennicke et al. | 425/178 |
| 3,635,630 | 1/1972 | Greene | 425/2 |
| 4,069,000 | 1/1978 | Hampshire | 425/395 |
| 4,182,507 | 1/1980 | Bekey et al. | 425/DIG. 11 X |
| 4,218,205 | 8/1980 | Beu | 425/180 |
| 4,359,435 | 10/1982 | Kogure | 425/DIG. 11 X |

FOREIGN PATENT DOCUMENTS

| | | |
|---|---|---|
| 0004844 | 10/1979 | European Pat. Off. . |
| 596128 | 3/1923 | France . |
| 876499 | 10/1940 | France . |
| 60-127112 | 7/1985 | Japan . |
| 61-10655 | 1/1986 | Japan . |
| 61-76149 | 4/1986 | Japan . |
| 61-263447 | 11/1986 | Japan . |
| 63-220861 | 9/1988 | Japan . |
| 2399070 | 9/1925 | United Kingdom . |
| 987835 | 3/1965 | United Kingdom . |
| 1349797 | 4/1974 | United Kingdom . |
| 2159457 | 12/1985 | United Kingdom . |

Primary Examiner—Jay H. Woo
Assistant Examiner—Robert B. Davis
Attorney, Agent, or Firm—Oblon, Spivak, McClelland, Maier & Neustadt

[57] ABSTRACT

A flask used with a method for making resin dental plates includes a splittable flask body having an upper lid member, a tray member and a lower lid member, all formed of a material through which microwaves are transmittable, an injection attachment to be mounted in place through a mounting hole between the tray member and the lower lid member and having an axial resin injection hole, and a sprue-opening closure member to close up the resin injection hole in the injection attachment, the flask body being provided in the vicinity of its side edge with at least two through-holes through which bolts of tightening mechanism are to be inserted. The tightening mechanism includes bolts and nuts, each formed of a material through which microwaves are transmittable, and the injection attachment having its outside shaped to fit into a recess formed at one end of the cylinder filled therein with a pasted resin.

7 Claims, 4 Drawing Sheets

METHOD FOR MAKING RESIN DENTAL PLATES AND FLASKS This application is a continuation of application Ser. No. 07/430,573, filed on Nov. 1, 1989, now abandoned.

BACKGROUND OF THE INVENTION

1. Field of the Invention

The present invention provides an apparatus for making resin dental plates of full or partial dentures and a dental plate-making flask, which is used for carrying out said method.

2. Description of the Prior Art

Flasks used to prepare resin dental plates making use of the irradiation of microwaves involve a flask formed of fiber-reinforced synthetic plastic (hereinafter FRP for short) (Japanese Patent Application Laid-Open No. 61-263447) which is preferably used for carrying out a method for making dental plates using a thermally polymerizable resin as a dental plate (Japanese Patent Application Laid-Open No. 61-76149) and an FRP flask for a gypsum mold or a flask (Japanese Patent Application Laid-Open No. 63-220861) formed of a metal material such as stainless steel and/or a ceramic material which is proposed in view of a strength problem with such a FRP flask. Usually, a flask formed of such materials is provided at the center of its upper or lower lid with a sprue opening, as disclosed in Japanese Utility Model publication No. 61-10655, through which a pasted resin is cast into a gap or gaps for a dental plate formed of gypsum placed therein.

The strength problem with the above FRP flask is that a position of the sprue opening, through which a pasted resin is injected into the gap in the dental plate formed of gypsum placed in the flask, is located at the center of the upper or lower lid of the flask. In order to allow the pasted resin to prevail throughout the dental plate gap, it is essentially required to increase the length of the sprue to satisfy the need of providing various branchings of a passage through which the pasted resin flows. Consequently, a pressure under which the pasted resin is to be filled has to be increased, resulting in increased load so that this may pose a safety problem to the FRP flask. This is the reason why the FRP flask cannot be used as a resin injection type of flask. In view of this, it has been proposed to use a flask formed of a metal or ceramic material. A problem with a flask formed of a metal material is, however, that microwaves are reflected off the metal, producing an undesirable influence upon the process involved (e.g., unpolymerized matter being left as such). A problem with a flask formed of a ceramic material is, on the other hand, that it may not only crack or break, when it is dropped or receives an impact, but is also expensive.

SUMMARY OF THE INVENTION

The fabrication of resin dental plates for full or partial dentures with the application of microwave irradiation involves such various problems as mentioned above. A primary object of the present invention is to provide an all-out solution to the-state-of-the-art problems by a method for making resin dental plates for full or partial dentures with a similar FRP (or possibly an engineering plastic) flask as heretofore used, making use of microwave irradiation, and a flask for making dental plates, which is preferably used for carrying out said method.

As a result of extensive and intensive studies made by the present inventor with a view to achieve the above object, it has been found that if a flask body is formed of such material as FRP or engineering plastics heretofore used in the art through which microwaves are transmittable, and includes an injection attachment having therein a resin injection hole on its side that is of so short a height relative to its plane extent (area) that no strength problem arises at all, it is then possible to connect the resin injection hole in the injection attachment to a temporal dental plate with a short sprue. It has also been found that if the resin injection hole in the injection attachment is closed up with a sprue opening closure member after the injection of resin, it is then possible to make much use of the advantage of the short-time polymerization of resin using microwaves. On the basis of such findings, the present invention has been accomplished:

BRIEF DESCRIPTION OF THE DRAWINGS

The present invention will now be explained specifically but not exclusively with reference to the accompanying drawings, in which.

DESCRIPTION OF THE INVENTION

Figure 1:
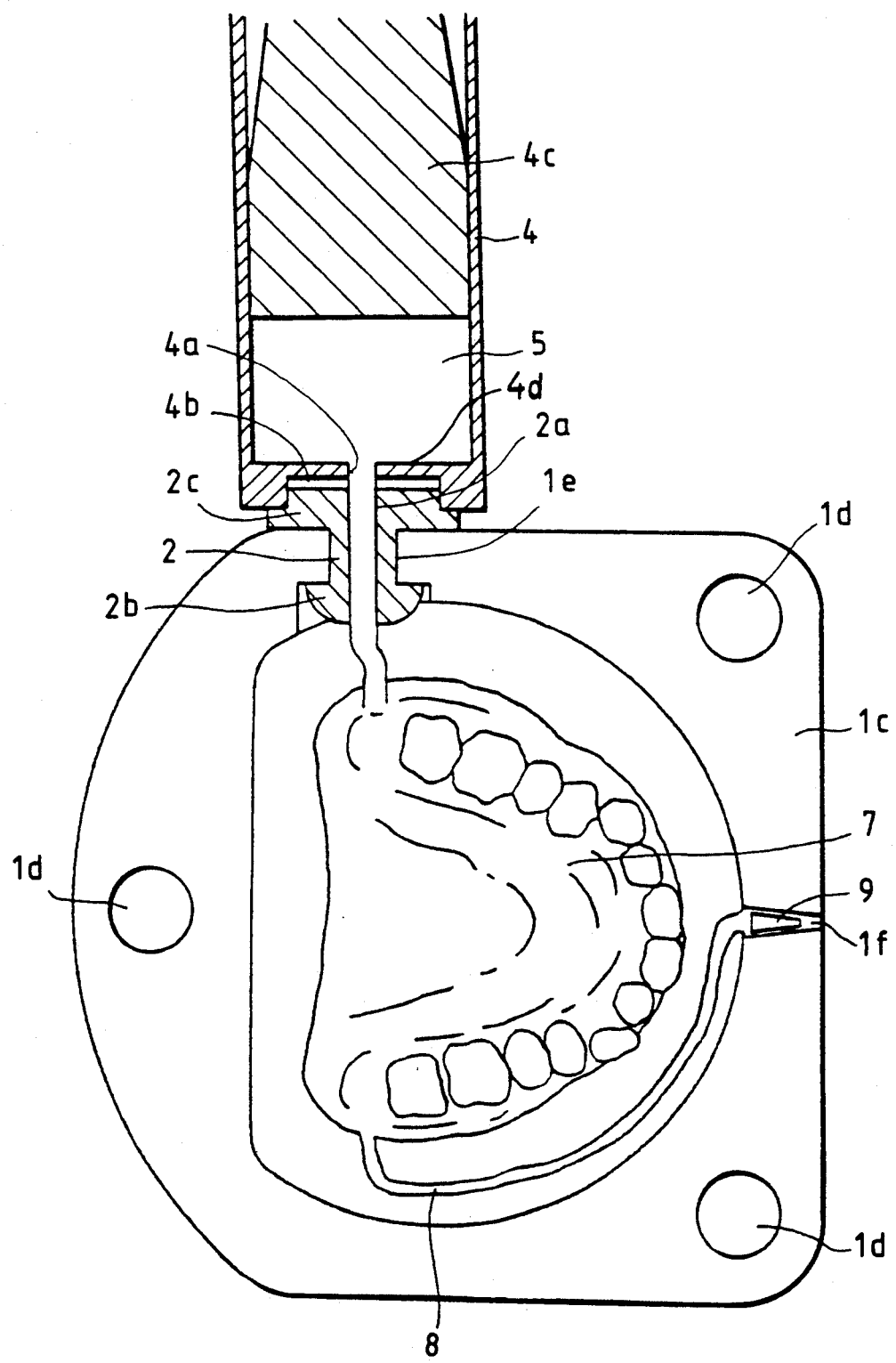
FIG. 1 is a longitudinally sectioned view showing the arrangement of the main parts for carrying out the method of the present invention.
Figure 2:
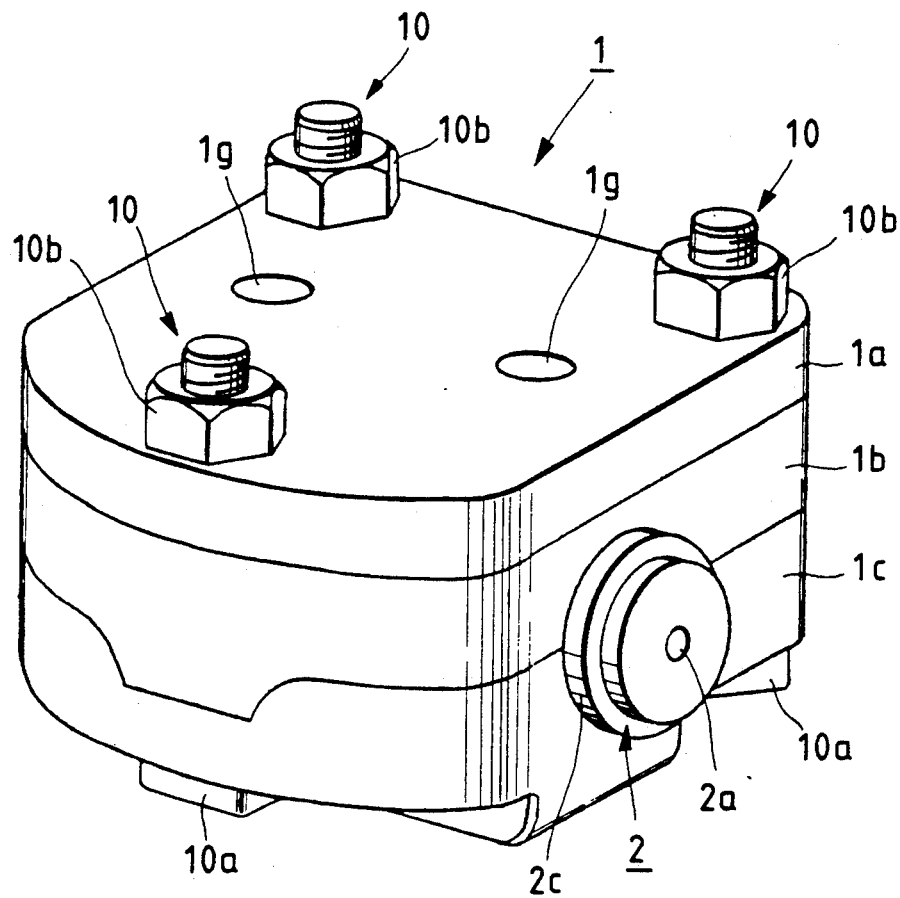
FIG. 2 is a perspective view illustrative of one embodiment the flask for making dental plates according to the present invention.

Referring to the drawings, a flask body, shown generally at 1, includes an upper or top lid member 1a, an intermediate tray member 1b and a lower or bottom lid member 1c, all formed of a microwave-transmittable material such as FRP or engineering plastics. The flask body 1 is provided with at least two (three in the illustrated embodiment) through-holes 1d in the vicinity of its peripheral edge, through which bolts 10a of tightening means 10 (to be described just below) are to be inserted to tighten the three members together into an integral assembly. Each of the tightening means 10 is comprised of a bolt 10a and a nut 10b, both formed of a synthetic plastic again transmittable with respect to microwaves. On its side, viz., between the tray member 1b and the lower lid member 1c, the flask body 1 includes a mounting port 1e, which is to receive an injection attachment 2 for the injection of a pasted resin 5 to form a resin dental plate as will be described later, and a vent port if which is provided if needed, so as to allow for the escape or discharge an amount of air from a zone through which a pasted resin 5 is injected from that mounting port 1e. The upper lid member 1a is provided with gypsum overflow holes 1g, usually two, for overflowing secondary gypsum which is to invest therein a gypsum model fixedly placed within the lower lid member 1c and including a temporary dental plate. Preferably, the mounting port 1e in the flask body 1 is comprised of axially aligned cut-outs provided in the tray and lower lid members 1b and 1c respectively so as to make the injection attachment 2 detachable. Upon being aligned with each other, the cut-outs just form the mounting port 1e through which the injection attachment 2 is held in place. Preferably, the vent port 1f, which is to be provided in the flask body 1 if needed, is tapered convergently toward its outermost end and receives therein a vent sealing member 9 which is tapered in a similar manner as mentioned above and has its thinner end directing outwardly, and as the resin injected through a resin injection hole 2a in the injection attachment 2 is filled to a position of the vent sealing member 9, the vent sealing member 9 is forced into close contact with the vent port 1f to automatically prevent outflow of the injected resin.

Figure 3:
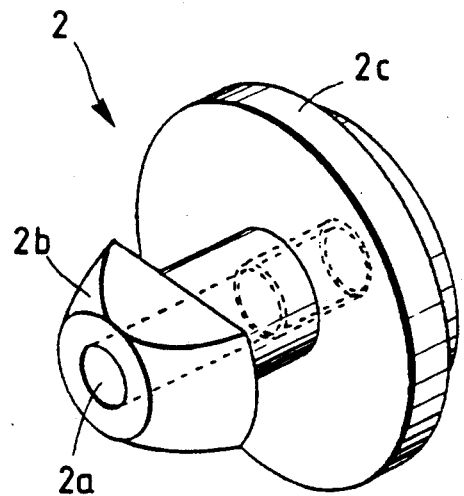
FIG. 3 is a perspective view illustative of an injection attachment to be mounted on the flask of FIG. 2.

The injection attachment 2 is detachably held in place through the mounting port 1e formed through the side of the flask body 1. As illustrated in FIG. 3, this injection attachment 2 includes through its axis a resin injection hole 2a, which is to communicate with the interior of the flask body 1, when attached to the mounting port 1e in the flask body 1. The injection attachment 2 is further provided on both sides thereof with inner and outer stopper members 2b and 2c, which are positioned in opposite relation to sandwich therebetween the wall section of the side of the flask body 1. Preferably, the outer stopper member 2c is fitted into a dent or recess 4b formed at one end of an end wall 4d of a cylinder 4, which stores therein an amount of the pasted resin 5 to be injected through the resin injection hole 2a in the injection attachment 2 into the flask body 1, so that a resin outlet hole 4a provided through the one end of the cylinder 4 can automatically communicate with the resin injection hole 2a extending axially through the injection attachment 2. Again preferably, the injection attachment 2 is formed of a material through which microwaves are transmittable, as is the case with the flask body 1. It is understood, however, that little or no problem arises even when the injection attachment 2 is formed of a material which reflects off microwaves, because it is smaller in size than the flask body 1. Once the paste resin 5 has been injected by a plunger 4c from within the cylinder 4 into the flask body 1 through the resin outlet hole 4a and then the resin injection hole 2a in the injection attachment 2, the flask is transferred to the next microwaves irradiation step, while the injection attachment 2 remains attached in place. For that reason, it is preferred that the injection attachment 2 is provided separately from the flask body 1 and be easily replaceable, because it is unlikely to be reusable due to the polymerization and curing of the pasted resin present in the resin injection hole 2a at the microwaves irradiation step.

Figure 4:
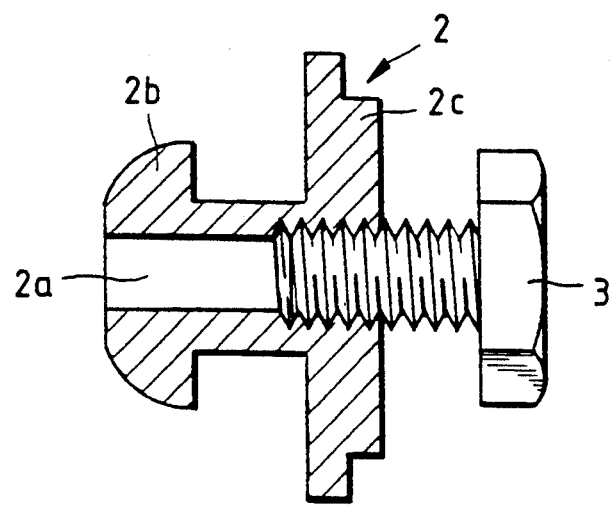
FIG. 4 is a sectional view illustrating a sprue-opening closure member fixedly disposed on the outside of the injection attachment of FIG. 3.

As illustrated in FIG. 4, a sprue-opening closure member 3 is provided to close up the resin injection hole 2a in the injection attachment 2, after the pasted resin 5 has been injected into the flask body 1.

Again preferably, both the sprue-opening closure member 3 and the vent sealing member 9 are formed of a material through which microwaves are transmittable for the reason mentioned earlier in connection with the the injection attachment 2. It is noted, however, that little or no problem arises even though they are formed of a material which reflects off microwaves.

Reference will now be made as to how to carry out the method of the present invention with the arrangement described above and illustrated in the drawings.

A splittable flask is first provided, which comprises the splittable flask body 1 comprised of the upper lid member 1a, tray member 1b and lower lid member 1c, all formed of a material through which microwaves are transmittable, the injection attachment 2 to be mounted in place through the mounting port 1e between the tray member 1b and the lower lid member 1c and having the axial resin injection hole 2a, and the sprue-opening closure member 3 to close up the resin injection hole 2a in the injection attachment 2. Then, a gypsum model having therein a waxed-up temporary dental plate 7 is fixedly positioned with primary gypsum in the lower lid member 1c of the flask body 1, and a gypsum remover is applied on the surfaces of the gypsum model and fixed primary gypsum. In order to previously assure a sprue and a vent in this case, the temporary dental plate 7 is connected to the resin injection hole 2a in the injection attachment 2 by means of a sprue member 6 comprising a commercially available wax rod of a constant diameter, while it is joined to the vent port 1f by means of a vent member 8 comprising a wax rod of a constant diameter but slightly smaller than that of the sprue member 6. After the injection attachment 2 has been attached to the flask body 1, the flask is assembled with the investment of the temporary dental plate 7 in secondary gypsum. After curing of the secondary gypsum, the flask is divided at the boundary between the tray member 1b and the lower lid member 1c to remove the temporary dental plate 7, thereby forming a dental plate void and assuring a sprue for communicating the the resin injection hole 2a in the injection attachment 2 with the thus formed void as well as a vent. This may be achieved by wax casting of the sprue and vent members 6 and 8 respectively, when the wax forming the temporary dental plate 7 is cast. When the waxy sprue and/or vent members 6 and 8 respectively are not used, however, this may be achieved by cutting off the cured secondary gypsum at the predetermined position. In particular, the vent may be formed, as occasion demands. The reason is that there is no special need of providing the vent port 1f and vent sealing member 9, and a slight gap left between the tray member 1b and the lower lid member 1c can be used for such purposes.

Following such an operation, the injection attachment 2 is attached to the flask body 1. Where there is the vent port 1f through the side of the flask body 1, the vent sealing member 9 is put into the vent port 1f, followed by re-assembling of the flask. Then, the cylinder 4, which is provided with the resin outlet hole 4a at its one end and in which the previously pasted resin 5 is fed from a bag of polyethylene or other material filled therewith, is joined at said end to the outer stopper 2c of the injection attachment 2 to sufficiently inject the pasted resin 5 from the resin outlet hole 4a at the end of the cylinder 4 into a dental plate gap through the resin injection hole 2a in the injection attachment 2 and the sprue. Thereafter, the resin injection hole 2a in the injection attachment 2 is closed up with the sprue-opening closure member 3. Subsequently, the flask is positioned in its entirety within a microwave irradiation space, in which the injected resin is exposed to microwaves for a given time to cure it.

Thus, while the resin injection hole 2a in the injection attachment 2 is closed up with the sprue-opening closure member 3 and, more preferably, the vent port 1f is sealed up by the vent sealing member 9 with the application of pressure, the pasted resin 5 is irradiated with microwaves for a given time within a microwave irradiation space defined by an microwave oven (not shown) or other means, so that the pasted resin 5 can be polymerized and cured completely.

Figure 5:
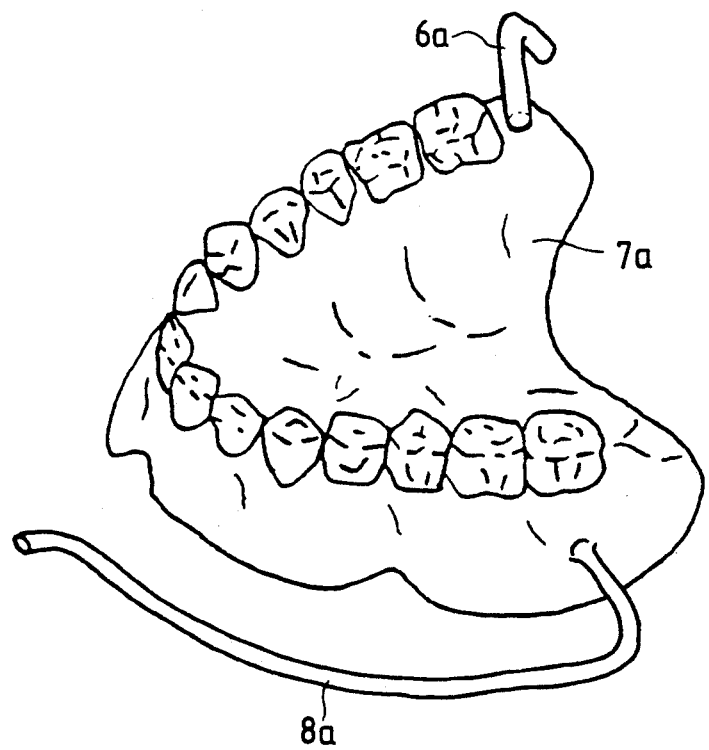
FIG. 5 is a perspective view of a resin dental plate with a sprue and a vent, which is made by the method of the present invention and is as removed from within a gypsum model.

With the thus prepared resin dental plate, it is possible to make the length and shape of the sprue 6a relatively short and simple, as depicted in FIG. 5 showing one example of the dental plate 7a which is removed. With the thickness of the vent 8a per case in mind, there is no special need of providing the vent port 1f and vent sealing member 9 and a slight gap left between the tray member 1b and the lower lid member 1c can be used to this end.

EMBODIMENTS

Figure 6:
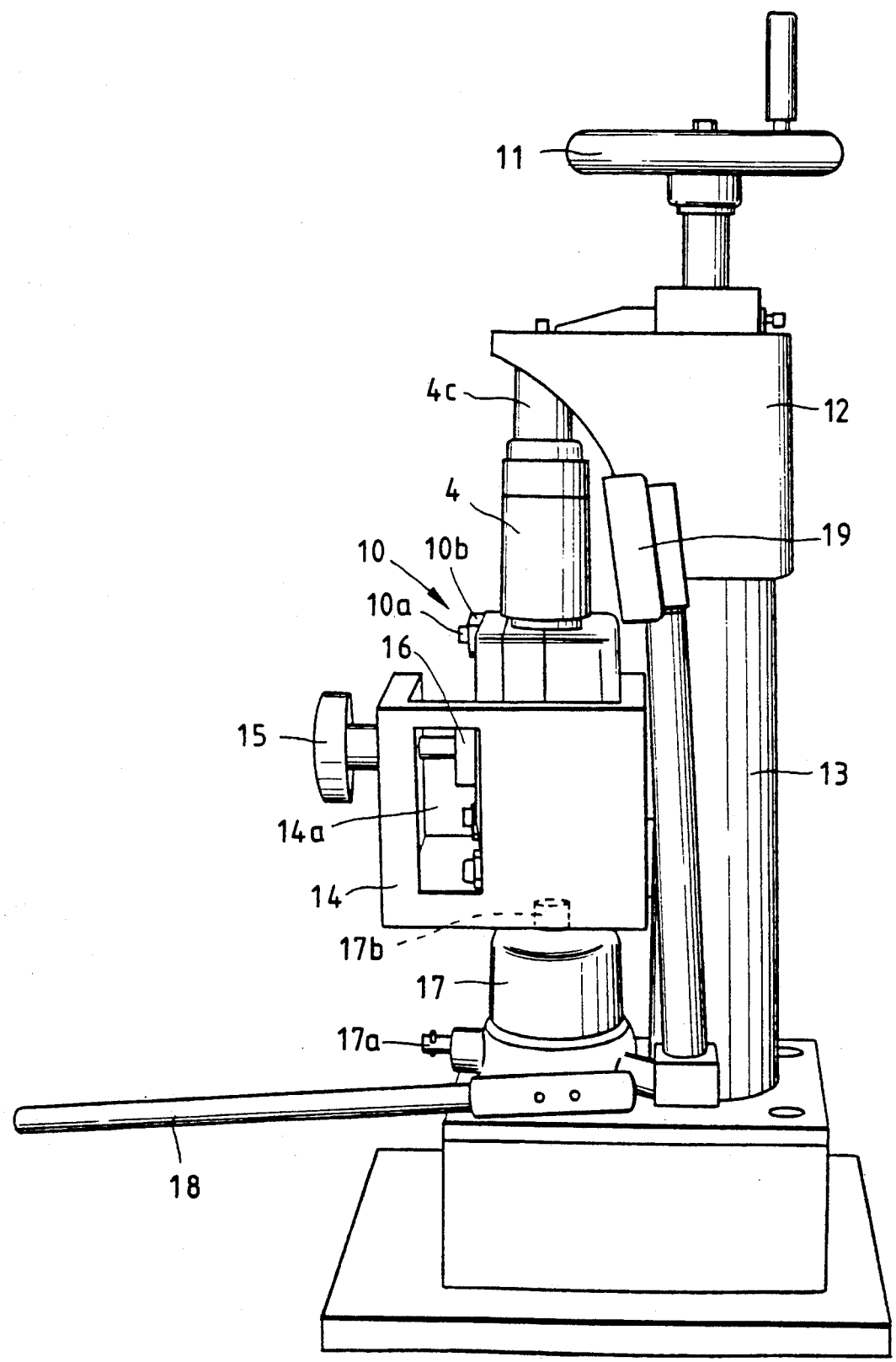
FIG. 6 is a perspective view showing a pasted resin being injected into the flask for making dental plates according to the present invention with an injector.

FIG. 6 is a view illustrating an injector arrangement developed especially for carrying out the method of the present invention and having functions suitable to this end. Such an arrangement need not be used, if satisfactory results are obtained with a commercially available pressing machine with a pressure gauge. In what follows, however, reference will be made to the preparation of a resin dental plate with the injector arrangement shown in FIG. 6.

A handle 11 is provided to displace a plunger support 12 having a plunger 4c vertically along a shaft 13. A resin outlet hole 4a at one end of a cylinder 4 having therein a pasted resin 5 is positioned such that it communicates with a resin injection hole 2a in an injection attachment 2 of a flask body 1 placed on a flask support table 14. Then, the handle 11 is turned to lower the plunger 4c down to a position at which it provides slight pressure to the pasted resin 5 within the cylinder 4. In this state, the flask body 1 is temporarily tightened up by tightening means 10. Subsequently, a knob 15 provided on the flask support table 14 is turned to achieve substantially axial alignment of the plunger 4c, cylinder 4 and injection attachment 2, after which the flask body 1 is fixedly positioned on the flask support table 14 with flask fixing means 16 mounted at the opposite end of the knob 15. Finally, the flask body 1 is tightened up by the tightening means 10 to assemble the upper lid member 1a, tray member 1b and lower lid member 1c into one piece in a well-balanced state. It is thus convenient to provide a cut-out 14a on the side of the flask support table 14 for the purpose of ensuring smooth handling of a tool (not shown), when the flask body 1 is finally tightened up by the tightening means 10. It is also preferable that the shaft 13 is provided with a longitudinal groove to prevent vibration of the flask support table 14 and a projection to fit into said groove is provided on the side of the flask support table 14 facing the shaft 13.

The flask support table 14 of such a structure is fixedly provided on its bottom with a jack shaft 17b of a hydraulic jack 17. After set up as mentioned above, a jack lever 18 is used to put the hydraulic jack 17 into operation, thereby jacking up the flask support table 14 on which the flask body 1 is placed. At this time, it is possible to prevent over- or under-charging of the pasted resin 5 by taking readings on the pressure gauge 19. To lower the flask support table 14, a pressure drain 17a may be turned to release pressure from within the jack.

EFFECTS OF THE INVENTION

With the method for making resin dental plates according to the present invention as detailed above, a series of operations can be carried out for a very short period of time, since it is possible to polymerize and cure a resin dental plate with the irradiation of microwaves making use of an microwave oven, etc. by a single filling of a pasted resin into a gap for the dental plate placed in the flask. Thus, it is possible not only to omit about three swaging steps of a conventional swaging process but also to dispense with deflashing and other steps that have to be carried out in the conventional swaging process. This has an advantage of perfectly eliminating such problems as ill working environments attributable to the volatilization of monomers from the pasted resin and deteriorated fitness of the mucosal surface of the resin dental plate which is again due to the volatization of monomers and poses a quality problem. Another advantage is that the resin dental plate can be polymerized and cured perfectly, since there is not left any unexposed portion of the resin by microwaves due to the fact that the flask body, tightening means and so on are all formed of a material based on synthetic plastics.

After the pasted resin has been injected into the flask, the resin injection hole in the injection attachment is closed up by the sprue-opening closure menber, followed by microwave irradiation. This ensures that the polymerization and curing of the resin takes place in a state where the internal pressure is maintained, since it is unlikely that the pressure under which the resin has been injected may escape from the resin injection hole. Thus, the obtained polymer or the resin dental plate is free from any air bubbles and so excels in physical properties such as density. Additionally, the obtained resin dental plate has a much improved fitness, since its deformation due to polymerization shrinkage is reduced or limited.

In terms of manipulatability, the present invention makes it possible to reduce the length of polymerization and curing time of resin to about three minutes, whereas as long as 2 hours are required for the polymerization and curing of resin in a conventional manner. The present invention also ensures that the length and shape of the sprue can be reduced and simplified, since the inlet hole for injecting a pasted resin is located through the side of the flask in the process of making a resin dental plate. Thus achievable are a reduction in the length of polymerization and curing time of a dental plate-forming resin that is the greatest merit of the polymerization and curing by microwaves and an improvement of fitness by such short-time polymerization. To add to this, so considerable improvements are introduced with respect to manipulatability that a nonmetallic flask or pressing machine so far owned by operators can be used as such, thus avoiding waste.

The flask according to the present invention possesses such various merits as mentioned above, is suitable for carrying out the method according to the present invention, and has an advantage of being easy and inexpensive to make.

Thus, the present invention provides an epoch-making method capable of preparing resin dental plates in an efficient and simple manner and a flask used for carrying out such a method, and so makes a great contribution to the advancement of dentistry.

What is claimed is:

1. A flask comprising:
   a splittable flask body which comprises an upper lid member, a tray member and a lower lid member, all formed of a material through which microwaves are transmittable,
   an injection attachment mounted on a mounting port formed of axially aligned cut-out portions of said tray member and said lower lid member and having an axial resin injection hole, and a sprue-opening closure member for closing said resin injection hole in said injection attachment,
   a cylinder filled with a pasted resin and a plunger positioned in said cylinder for injecting said resin into said resin injection hole, said cylinder having an end wall with an outlet hole formed therein and a recessed portion formed on a side of said wall opposite said plunger; and
   said flask body being provided in the vicinity of a side edge thereof with at least two through-holes and tightening means inserted into said through holes, wherein said tightening means comprises securing members, each formed of a material through which microwaves are transmittable, and wherein said injection attachment is provided with a resin injection hole and with inner and outer stopper members formed of a material through which microwaves are transmittable in such opposite relation as to hold therebetween a wall region of the side of said flask body, said outer stopper member being positioned in said recessed portion formed at said one end of said cylinder.

2. A flask as claimed in claim 1, wherein said flask body is formed of a fiber-reinforced synthetic plastic, said injection attachment is formed of a synthetic plastic, and said tightening means are formed of a synthetic plastic.

3. A flask as claimed claim 2, wherein said flask body is provided, through its side with at least one vent port.

4. A flask as claimed in claim 3, wherein said vent port formed through the side of said flask body is tapered convergently toward its outermost end, and a bent sealing member having a taper corresponding to that of said vent port is inserted therein such that its thinner end directs outwardly.

5. a flask as claimed in claim 1, wherein said flask body has in a side portion thereof at least one vent port wherein said vent port is tapered convergently toward an outermost end portion thereof, and wherein a vent sealing member having a taper corresponding to that of said vent port is positioned therein such that a thinner end thereof is directed outwardly.

6. A flask as claimed claim 1, wherein said flask body is provided through its side with at least one vent port.

7. A flask as claimed in claim 6, wherein said vent port formed through the side of said flask body is tapered convergently toward its outermost end, and a bent sealing member having a taper corresponding to that of said vent port is inserted therein such that its thinner end directs outwardly.

* * * * *